(12) United States Patent
Wolfe et al.

(10) Patent No.: US 6,660,734 B1
(45) Date of Patent: Dec. 9, 2003

(54) OXAZINONES HAVING ANTIBACTERIAL ACTIVITY

(75) Inventors: Saul Wolfe, North Vancouver (CA); Christiana Akuche, New Westminster (CA); Stephen Ro, Beverly Hill, CA (US)

(73) Assignee: Simon Fraser University, Burnaby (CA)

( * ) Notice: Subject to any disclaimer, the term of this patent is extended or adjusted under 35 U.S.C. 154(b) by 0 days.

(21) Appl. No.: 10/055,831

(22) Filed: Jan. 22, 2002

Related U.S. Application Data

(62) Division of application No. 09/102,285, filed on Jun. 22, 1998, now Pat. No. 6,399,600.
(60) Provisional application No. 60/050,456, filed on Jun. 23, 1997.

(51) Int. Cl.[7] .................... A61K 31/535; C07D 273/04
(52) U.S. Cl. ................ 514/228.8; 514/230.8; 544/63; 544/68
(58) Field of Search .................. 514/228.8, 230.8; 544/63, 68

(56) References Cited

FOREIGN PATENT DOCUMENTS

JP     62215585    *   9/1987

OTHER PUBLICATIONS

CAS Abstr.108:186753–1988:186753; also cited as JP 62215585 Sep. 1987;Yoshioka, Koichi et al.*
Chemical Abstract DN 108:186753.*
"Hydroxylamine Derivatives", *Chemical Abstracts*, 70: 66520h (1970).
"Reaction of γ–bromoacetoacetyl bromide with N–phenyl-hydroxylamine derivatives: synthesis of 1,2–oxazine derivatives," *Chemical Abstracts* 92:76427 (1979).
Barlos, K. et al.; "Anwendung von N–Trirylmeth. zur Darst. v.biologisch u.synthetisch inter Hetero", *Liebgs. Ann. Che*. pp. 1127–1133 (Mar. 1988).

(List continued on next page.)

*Primary Examiner*—Mukund J. Shah
*Assistant Examiner*—Sudhaker B. Patel
(74) *Attorney, Agent, or Firm*—Lahive & Cockfield, LLP; Elizabeth A. Hanley, Esq.; Cynthia M. Soroos

(57) ABSTRACT

The invention relates to novel oxazinones designed to bind to the penicillin receptor, methods of synthesizing the compounds, and the use of the compounds as antibacterial agents. The compounds have the general formula (I)

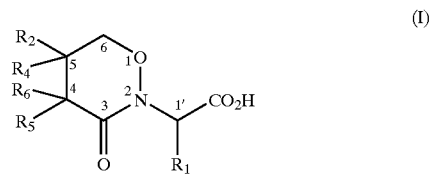

Preferably the compounds have a carboxyethyl or a substituted carboxymethyl substituent at the 2-position and a hydroxyl group at the 5-position and have a molecular shape suitable for binding to and reacting with the active site of a pencillin-recognizing enzyme. The compounds are synthesized by condensing a carboxyl-protected N-hydroxy amino acid with a 3-hydroxyprotected-4-bromobutanoic acid to form a a doubly protected N-hydroxy N-acylamino acid, which is cyclized with an organic base to yield a: doubly protected 1,2-oxazin-3-one. The protecting groups are then removed to provide an antibacterial agent.

11 Claims, 5 Drawing Sheets

OTHER PUBLICATIONS

Barlos et al., "Anwendung von N–Tritylmethionin zur Darstellung von biologisch und synthetisch interessanten Heterocyclen", *Liebigs Ann. Chem*, pp. 1127–1133 (1988) [German].

Hora, "Synthesis of 7–.alpha.–Acetylthio–(6'R)–6'Methyl–3'–Oxotetrahydro–1,1'2'—Oxazino [4',5':13.beta., 17.beta.]–18 Norandrost–4–En–3–One", *Collection Czechoslov. Chem. Commun.* 32: 2820–2825 (1967).

Hora, "Synthesis of Steroidal Tetrahydro–1,2–Oxazine–3–One Derivatives", *Collection Czechoslov. Chem. Commun.*, 30: 70–80 (1965).

Karpeiskii, et al., "The Mechanism of Reaction of Cycloserine and Related Compounds with Aspartate–Glutamate Transaminase", *Biokhimiya*, 28(2): 345–352, (Mar.–Apr., 1963).

Khomutov, "Synthesis of O–Substituted Hydroxylamines", *Zhurnal Obshchei Khimii*, 31(6): 1992–1995, (Jun. 1961).

Khomutov et al., "The Relationship Between Biological Activity and Chemical Properties", *Biokhimiya*, 26(5): 772–781, (Sep.–Oct. 1961).

Khomutov et al., "Synthesis of Tetrahyro–1,2–Oxazin–3–One", *Izvestiya Akademii Nauk SSSR, Otdelenie Khimicheskikh Nauk*, 6: 1074–1076, Jun. 1962; *Chemical Abstracts* 13754a, (1962).

Khumotov et al., "On Some Cycloserine Derivatives Possessing Antituberculose activity", *Voprosy Meditsinskoi Khimii*, 8(389), (1962) [English Abs. only.].

Khomutov et al., "Synthesis of Cyclocanaline (Homocycloserine) and Related Compounds", *Izvestiya Akademii Nauk SSSR*, 12: 2161–2166, Dec., (1962); Chemical Abstracts 13944 (1963).

Kuehl, F.A. et al. "Communications to the Editor: D–4–Amino–3–Isoxazolidone, A New Antibiotic" *J. Am. Chem. Soc.*, vol. 77, pp. 2344–23451 (Apr./Jun. 1955).

Procter et al., "β–Lactams From Tetrahydro–1,2–Oxazine–3,6–Diones, and a Labelling Study of the Product Stereochemistry", *Tetrahedron*, 51(47): 12837–12842 (1995).

Rosenthal et al., "Insecticidal Properties of Some Derivatives of L–Canavanine", *J. Agric. Food Chem.*, 43:2728–2734 (1995).

Tabei, Katsumi et al. Chem. Pharm. Bull. 27(8):1842–6 (1979).

Tabei, Katsumi et al., "Organic Sulfites Containing a 1,2–Oxazine Ring", *Chem. Pharm. Bull.*, 28(1): 330–336 (1980).

Wolfe et al., "Hydration of the Carbonyl Group. A Theoretical Study of the Cooperative Mechanism", *J. Am. Chem. Soc.*, 117: 4240–4260 (1995).

Wolfe, Saul "1992 Lemieux Award lecture: Studies related to the penicillin receptor" *Canadian J. Chem.* 72:1014–32 (1994).

Wolfe, Saul et al. "A semiempirical molecular orbital study of the methanolysis of complex azetidinones. A combined MM and QM analysis of the interaction of $\Delta^2$–and $\Delta^3$–cephems with the penicillin receptor" *Canadian J. Chem.* 72:1044–50 (1994).

Wolfe, Saul et al. "Ab initio molecular orbital calculations on the neutral hydrolysis and methanolysis of azetidinones, including catalysis by water. Relationship to the mechanism of action of β–lactam antibiotics" *Canadian J. Chem.* 72:1033–43 (1994).

Wolfe, Saul et al. "Conformation–activity relationships and the mechanism of action of penicillin" *Canadian J. Chem.* 66(11):2733–50 (1988) [English Abs. only].

Wolfe, Saul et al. "Interactive design and synthesis of a novel antibacterial agent" *Canadian J. Chem.* 72(4):1051–65 (1994).

Wolfe, Saul et al. "MMPEN: Development and evaluation of penicillin parameters for Allinger's MMP2(85) programme" *Canadian J. Chem.* 66(11):2715–32 (1988).

Wolfe, Saul et al. "MMPEP: Development and evaluation of peptide parameters for Allinger's MMP2(85) programme, including calculations on crambin and insulin" *Canadian J. Chem.* 66(11):2687–2702 (1988).

Wolfe, Saul et al. "Phenceptin: a biomimetic model of the phenytoin receptor" *Canadian J. Chem.* 66(11):2751–62 (1988).

Wolfe, Saul et al. "Theoretical conformational analysis of peptides. Evolution of a strategy and its application to cholecystokinin analogs" *Canadian J. Chem.* 66(11):2703–14 (1988).

\* cited by examiner

OXAZINONES HAVING ANTIBACTERIAL ACTIVITY

This application is a divisional application of application Ser. No. 09/102,285 filed on Jun. 22, 1998 now U.S. Pat. No. 6,399,600 (CPA filed Dec. 15, 2000), Allowed, which claims benefit of provisional application No. 60/050,456, filed on Jun. 23, 1997. The contents of all of the aforementioned application(s) are hereby incorporated by reference.

TECHNICAL FIELD

This invention relates to novel compounds designed to bind to the penicillin receptor, to methods for preparing the novel compounds, and to the use of the compounds as antibacterial agents.

BACKGROUND

Many antibiotics act by interfering with the biosynthesis of bacterial cell walls.[1] The completion of bacterial cell wall synthesis is mediated by enzymes termed penicillin-binding proteins (PBPs)[2] which cross-link different peptidoglycan chains. In particular, PBPs link the penultimate D-Ala residue of a peptidoglycan terminating in a N-acyl-D-Ala-D-Ala moiety to the terminal amino group of a lysine residue of another peptidoglycan chain. Glycopeptide transpeptidase is an example of a PBP present in many bacteria.

All known PBPs contain a conserved Ser-X-X-Lys sequence at the active site. The β-lactam family of antibiotics, whose members include penicillins and cephalosporins, inhibit PBPs by forming a covalent bond with the active site serine residue. In the case of penicillin, the labile β-lactam ring reacts with the hydroxyl group of the active site serine to form an acyl-enzyme intermediate as shown in Scheme 1 below.

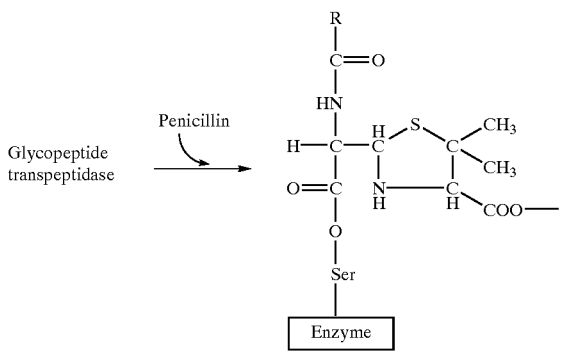

Scheme 1

The enzyme is therefore unable to carry out the final step in the biosynthesis of the bacterial cell wall.[3] As a result, the wall is weakened, becomes permeable to water, and the bacterial cell swells, bursts, and dies.

The simplest kinetic description of the reaction between a bacterial enzyme (Enz) and a β-lactam antibiotic is given in Scheme 2 below:

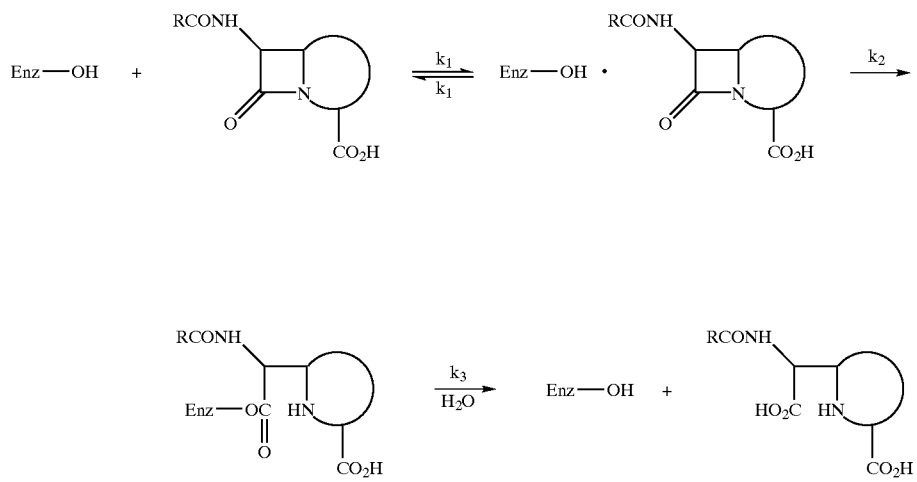

Scheme 2

In addition to the PBP's, many bacteria also produce a second type of penicillin-recognizing enzyme, known as a β-lactamase. PBPs and β-lactamase enzymes exhibit the same kinetics as set forth in Scheme 2 above, but with different rate constants.[4] This difference in rate constants has important consequences. In the case of the PBP's, $k_2 \gg k_3$ (i.e the formation of the acyl-enzyme is much faster than its hydrolysis). The result is that the enzyme is inhibited, and antibacterial activity may be observed. In the case of a β-lactamase, $k_2 \approx k_3$ (i.e. the formation and hydrolysis of the acyl enzyme proceed at comparable rates). These kinetics lead to regeneration of the enzyme, and inactivation of the antibiotic as a result of the net hydrolysis of the β-lactam bond in the deacylation step. The latter sequence of reactions comprises the principal mechanism of bacterial resistance to β-lactam antibiotics. Useful antibacterial activity is considered to require $k_2/k_1 \geq 1000\ M^{-1}\ sec^{-1}$ and $k_3 \leq 1 \times 10^{-4}\ sec^{-1}$.

Resistance to antibiotics is a problem of much current concern.[5] Alternatives to existing antibiotics are invaluable when bacteria develop immunity to existing drugs or when patients are allergic to existing drugs (approximately 5% of the population is allergic to penicillin). Because of the relatively low cost and relative safety of the β-lactam family of antibiotics, and because many details of their mechanism of action and the mechanism of bacterial resistance are under-stood, one approach to the problem of resistance is to design new classes of compounds that will complex to and react with a penicillin-recognizing enzyme, and be stable to the hydrolysis step. In order to be effective, the antibacterial agent should have the ability to react Irreversibly with the active site serine residue of the enzyme.

The crystal structures of β-lactamase from *B. licheniformis, S. aureus* and *E. coli* (RTEM) suggest a chemical basis for resistance to β-lactam antibiotics (FIG. 1). Apart from the conserved Ser-X-X-Lys active site sequence, β-lactamase have a conserved Glu166 which participates in the hydrolysis of the acyl-enzyme. It appears that the hydroxyl group of the active site serine and the carboxyl group of Glu166 together with a water molecule are involved in the hydrolysis step. The inventors have found that, in water solvent, one "non-spectator" water molecule plays an active role in the carboxylic acid catalysis of ester hydrolysis.[6,7] The water molecule and the carboxyl group act in concert and this interaction is the source of bacterial resistance to β-lactam antibiotics. Drug design must therefore include a process for the removal or inactivation of this water molecule.

Numerous β-lactam antibiotics have been developed in the past which are structural analogues of pencillin and which complex to and react with penicillin-recognizing enzymes. Like penicillin, such antibiotics are presumed to be conformationally constrained analogues of the N-acyl-D-Ala-D-Ala peptidogly-can moiety, the O=C—N β-lactam bond being a bioisostere of the D-Ala-D-Ala peptide bond.[8] Effective antibacterial activity also requires a properly positioned carboxyl group or equivalent and a hydrogen-bonding hydroxyl or acylamino group. One of the inventors has previously designed a computer-implemented molecular modelling technique for identifying compounds which are likely to bind to the PBP active site and are therefore likely to exhibit antibacterial activity. This modelling technique is described in U.S. Pat. No. 5,552,543 issued Sep. 3, 1996, the disclosure of which is hereby incorporated by reference.

FIG. 2 summarizes comparative chemical reactivity results obtained using an improvement to the computer strategy described in the '543. Patent. The activation energies (kcal/mol) for the reactions of various ring systems with a hydroxyl group were calculated and compared to that of the bicyclic ring system of penicillin. The inventors have determined that these relative reactivities parallel exactly the relative antibacterial activities of all known classes of β-lactam compounds (as well as non-β-lactam compounds, such as Lactivicin[9] and the pyrazolidinone family of synthetic antibiotics[10], which are known to complex to and react with penicillin-recognizing enzymes). The ring system identified in FIG. 2 as A formed the basis for synthesis of novel compounds exhibiting antibacterial activity described in the '543 Patent. The present application is directed to novel oxazinone compounds based on the 1,2-oxazine ring system identified in FIG. 2 as B.

Some oxazinones having possible biological activity are known in the prior art. Khomutov et al synthesized tetrahydro-1,2-oxazin-3-one (Chemical Abstracts 13754a, 1962) and 4-benzamidotetrahydro-1,2-oxazin-3-one (chemical Abstracts 58, 13944b, 1963). The latter compound is also known as N-benzoyl-cyclocanaline. According to Khomutov, cyclocanaline is known to Inhibit glutamate-aspartate transaminase and exhibits activity against tuberculosis bacilli. The structure of cyclocanaline is shown in formula (A) below.

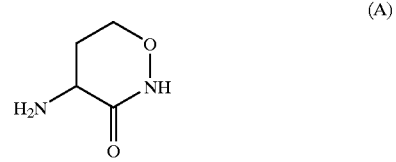

(A)

Frankel et al reported the synthesis of DL-cyclocanaline (4-amino-tetrahydro-1,2-oxazin-3-one) hydrochloride from canaline dihydrochloride in 1969 (J. Chem. Soc. (C) 1746–1749, 1969) and recognized that DL-cyclocanaline is a higher homologue of the antibiotic cycloserine.

Barlos et al reported the synthesis of S-4-(N-tritylamino)-tetrahydro-1,2-oxazin-3-one (also known as N-trityl-cylocanaline) in 1988 (Liebigs Ann. Chem. 1127–1133, 1988).

The inventors are not aware of any reports of cyclocanaline derivatives or other oxazines which have been previously recognized to be structural analogues of penicillin. The need has therefore arisen for a new class of oxazinones synthesized to exhibit antibacterial activity which satisfy the following structural requirements:
1. The compound will complex to the active site of a penicillin recognizing enzyme.
2. The compound includes a functional group that, when positioned properly at the active site of the enzyme, is able to react with the hydroxyl group of the active site serine by a mechanism and with a rate constant comparable to the mechanism and rate constant exhibited by penicillin or cephalosporin.
3. The resulting acyl-enzyme is stable and resistant to hydrolysis, thereby preventing regeneration of the bacterial enzyme at a significant rate.

SUMMARY OF INVENTION

In one aspect, the invention provides a compound selected from the group consisting of compounds having antibacterial activity represented by the general formula (I) and pharmaceutically acceptable salts thereof:

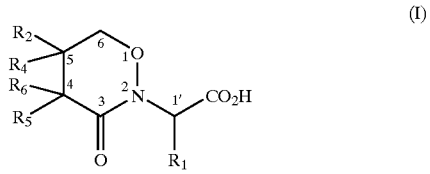

(I)

where $R_1$ is the side chain of a D- or L-alpha amino acid, $R_2$ is OH, $NH_2$, or $NHCOR_3$, $R_3$ is a substituent known to confer antibacterial activity when present in the side chain of a penicillin or cephalosporin, $R_4$ is H or loweralkyl, $R_5$ is one of OH, $NH_2$ or $NHCOR_3$ when $R_6$ is H, and $R_6$ is one of OH, $NH_2$ or $NHCOR_3$ when $R_5$ is H. Preferably $R_5$ and $R_6$ taken together comprise the oxygen of a carbonyl group which absorbs a water molecule found at the active site of a β-lactamase enzyme.

In one embodiment $R_2$ is OH, $R_1$, $R_4$, $R_5$ and $R_6$ are hydrogen and the compound has the S-configuration at C5. In another embodiment, the compound has the R-configuration at C5. The compound may have either the S-configuration or the R-configuration at C1'.

A process for the production of the compound represented by formula (I) is also provided comprising condensation of a carboxyl-protected N-hydroxy alpha-amino acid with a 3-hydroxy-protected-4-bromobutanoic acid, cyclization of the resulting doubly protected N-hydroxy-N-acylated alpha amino acid, and removal of the protecting groups. In one embodiment the carboxyl-protecting group is t-butyl, the hydroxyl-protecting group is 2-tetrahydropyranyl, the condensing agent is dicyclohexylcarbodiimide, the cyclization is performed with an organic amine, and the removal of the protecting groups is performed with trifluoroacetic acid.

The invention also pertains to a pharmaceutical composition comprising an effective amount of a compound according to formula (I) together with a pharmaceutically-acceptable carrier and a method of treatment of bacterial infection in a mammal, comprising the step of administering to a mammal in need of such treatment an effective amount of a compound according to formula (I).

BRIEF DESCRIPTION OF THE DRAWINGS

In drawings which illustrate embodiments of the invention, but should not be construed as restricting the spirit or scope of the invention in any way.

DESCRIPTION OF PREFERRED EMBODIMENTS

Figure 1:
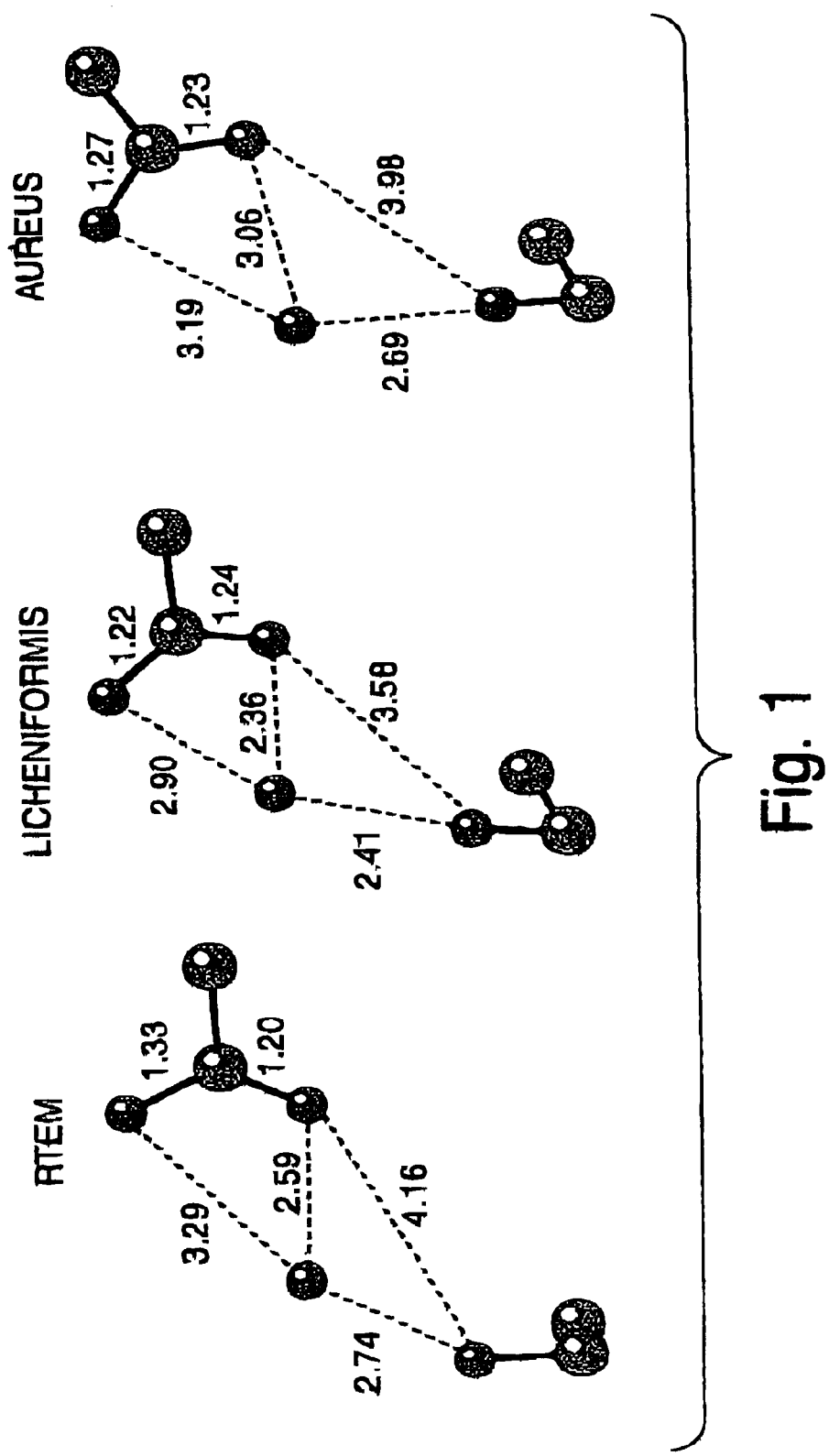
FIG. 1 is a portion of the crystal structures of the β-lactamases of *B. licheniformis*[11], *S. aureus*[12] and *E. coli*[13] showing the relationship between the hydroxyl group, the essential water molecule and the carboxyl group of Glu166.

This application relates to the synthesis and use of novel 1,2-oxazin-3-one compounds having antibacterial activity and represented by the general formula (I):

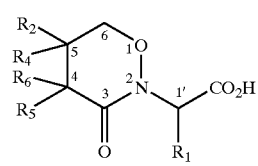
(I)

The compounds preferably have a carboxyethyl or substituted carboxymethyl substituent at the 2-position and a hydroxyl group at the 5-position. The compounds were designed using the computer-implemented molecular modelling technique described in U.S. Pat. No. 5,552,543 issued Sep. 3, 1996.

The proposed structural relationship between the N-acyl-D-Ala-D-Ala peptidoglycan moiety, penicillin and the 1,2-oxazin-3-one compounds of the present invention should be apparent by comparing formulas (B)–(D) below, the bold lines highlighting the structural similarities.

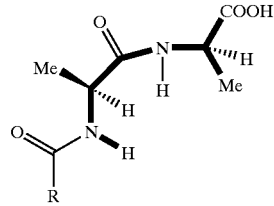
(B)

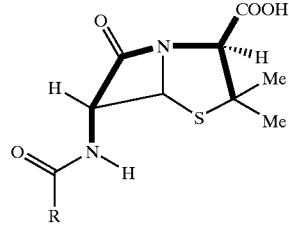
(C)

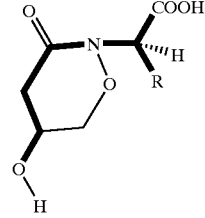
(D)

Both the (C) and (D) compounds are considered to be conformationally constrained analogues of the peptidoglycan moiety (which explains their ability to bind specifically to the active site of bacterial enzymes linking peptidoglycan chains). The oxazinone carbonyl group corresponds to the penicillin β-lactam carbonyl group; the hydrogen of the oxazinone hydroxyl group corresponds to the N—H hydrogen of the acylamino side chain of penicillin; and the carboxyl group of the carboxyethyl substituent of (D) corresponds to the C3-carboxyl group of penicillin.

As set forth in the following examples, two oxazinones exhibiting antibacterial activity have been successfully synthesized and chemically characterized, namely 2-carboxymethyl-5-hydroxy-1,2-oxazin-3-one and 2-[2-substituted carboxyethyl]-5-hydroxy-1,2-oxazin-3-one. These compounds are chemically stable, can be synthesized easily in large quantities from inexpensive and readily available starting materials, and exhibit antibacterial activity.

The chemical syntheses of 2-carboxymethyl-5-hydroxy-1,2-oxazin-3-one and 2-[2-substituted carboxyethyl]-5-hydroxy-1,2oxazin-3-one are summarized in Scheme 3.

Scheme 3

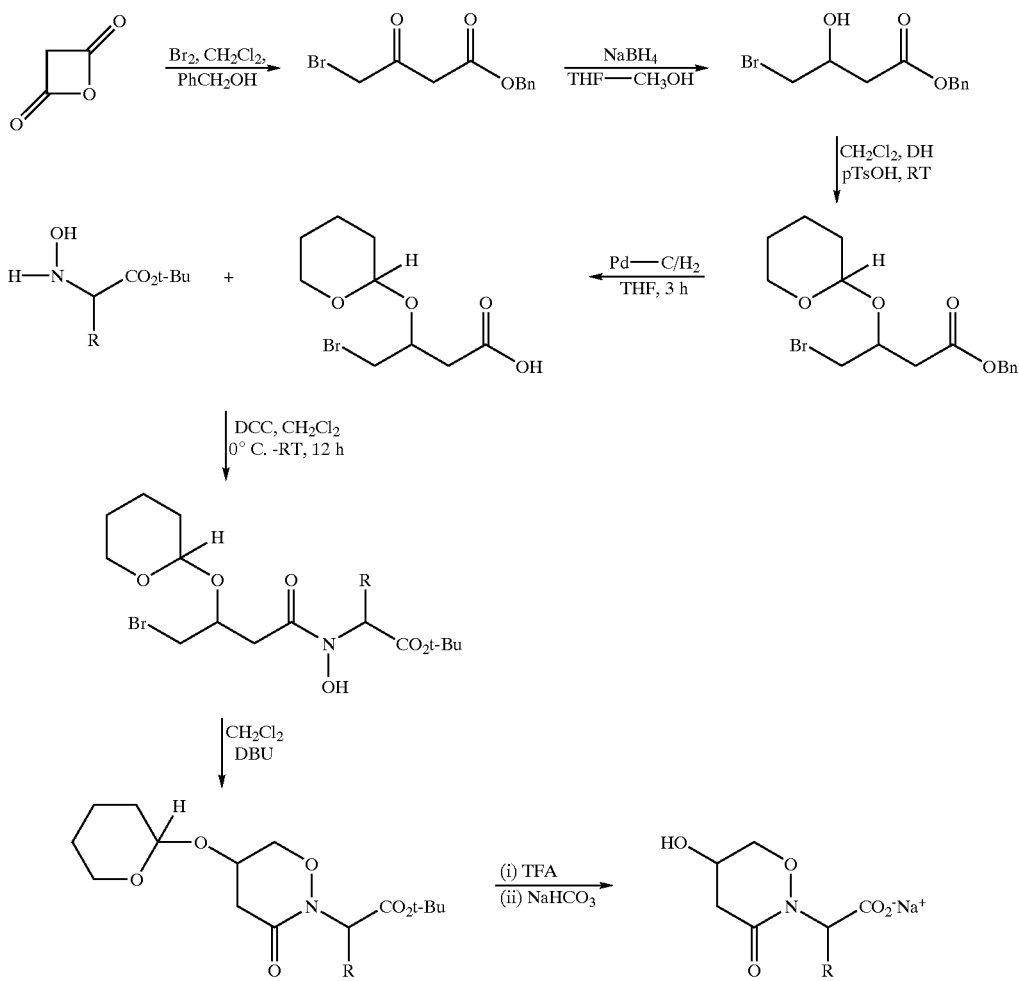

Briefly, a carboxyl-protected N-hydroxyamino acid is condensed with a 3-hydroxyprotected 4bromobutanoic acid to form a doubly protected N-hydroxy N-acylamino acid. In Example 1 below, the carboxyl-protected N-hydroxy amino acid is t-butyl N-hydroxyglycine. In Example 2 below, the carboxyl-protected N-hydroxy amino acid is t-butyl N-hydroxyalanine. The doubly protected N-hydroxy N-acylamino acid is cyclized with an organic base to yield a doubly protected 1,2-oxazin-3-one. The protecting groups are then removed to provide an antibacterial agent. In a preferred embodiment, the carboxyl and hydroxyl protection are, respectively, t-butyl and 2-tetrahydropyranyl, the condensing agent is dicyclo-hexylcarbodiimide, the cyclizing agent is diazabicycloundecene, and the deprotecting agent is trifluoroacetic acid.

EXAMPLE 1

2-Carboxymethyl-5-hydroxy-1,2-oxazin-3-one

Step 1. Benzyl γ-Bromoacetoacetate. Diketene (500 μL, 545 mg, 6.5 mmoles) was dissolved, under nitrogen, in dichloromethane (2 mL), cooled to −25° C., and treated dropwise with a solution of bromine (333 μL, 1.02 g, 6.5 mmoles) in dichloromethane (2 mL). After the addition was complete, the solution was stirred at −25° C. for 15 min, and benzyl alcohol (700 μL, 732 mg, 6.8 mmoles) was added dropwise. Stirring was continued for 15 min, and the solution was warmed to room temperature and evaporated. The residue was dissolved in diethyl ether (20 mL), washed successively with saturated sodium bicarbonate (2×20 mL), water (20 mL) and saturated sodium chloride (20 mL), dried over anhydrous magnesium sulfate and evaporated to give benzyl γ-bromoacetoacetate as a pale yellow oil (1.70 g, 97%) $^1$HMR (CDCl$_3$, δ): 7.36 (5H, m), 5.19 (2H, s), 4.02 (2H, s), 3.75 (2H, s). IR (neat): 3033, 1734, 1654 cm$^{-1}$. Mass spectrum (CI, m/z): 271, 273 (M+1, M+3), Calcd. for C$_{11}$H$_{11}$BrO$_3$: C48.69; H 4.05. Found: C 48.55; H 3.94.

Step 2. Benzyl-3-hydroxy-4Bromobutanoate. The product of step 1 (500 mg, 1.84 mmoles) was dissolved in a mixture of tetrahydrofuran (9 mL) and methanol (1 mL), the solution was cooled in an ice-bath, and sodium borohydride (72 mg, 1.90 mmoles) was added in one portion. Stirring was continued in the ice-bath for 15 min, and ethyl acetate (50 mL) and M hydrochloric acid (1.5 mL) were added. The aqueous layer was separated, extracted with ethyl acetate (20 mL), and the combined organic layers were washed with saturated sodium bicarbonate (40 mL), dried over anhydrous magnesium sulfate and evaporated to give benzyl 3-hydroxy-4-bromobutanoate (433 mg, 86%). $^1$HMR (CDCl$_3$, δ): 7.36 (5H, s), 5.17 (2H, s), 4.26 (1H, m), 3.50 (1H, dd, 5.0, 10.5 Hz), 3.47 (1H, dd, 5.6, 10.5 Hz), 3.06 (1H, d, 5.1 Hz), 2.72 (1H, dd, 5.0, 16.6 Hz), 2.69 (1H, dd, 7.3, 16.6 Hz). IR (neat):

3443, 3064, 1731, 1624 cm$^{-1}$. Mass spectrum (CI, m/z): 273, 275 (M+1, M+3). Calcd. for $C_{11}H_{13}BrO_3 \cdot 0.5H_2O$: C 53.75; H 5.88. Found: C 53.65; H 5.60.

Step 3. Benzal 3-[2-tetrahydropyranyloxy]-4-Bromobutanoate. The product of step 2 (845 mg, 3.09 mmoles) was dissolved in dichloromethane (10 mL), and dihydropyran (300 μL, 277 mg, 3.29 mmole) and p-toluenesulfonic acid monohydrate (3 crystals) were added. The solution was stirred at room temperature for 1.5 h. Diethyl ether (40 mL) was then added, and the solution was washed with saturated sodium bicarbonate (2×40 mL), dried over anhydrous sodium sulfate, and evaporated. Purification by column chromatography using ethyl acetate-hexanes (3:7) gave benzyl 3-[2-tetrahydropyranyloxy]4-bromobutanoate (1.07 g, 97%) as a 1:1 mixture of diastereoisomer. IR (neat): 3033, 1737 cm-1. Mass spectrum (CI, m/z): 357, 3539 (M+1, m+3). Calcd. for $C_{16}H_{21}BrO_4$: C 53.75; H 5.88. Found: C 53.65; H 5.60.

Step 4. 3-[2-Tetrahydropyranyloxy]-4-Bromobutanoic Acid. The product of Step 3 (73 mg, 0.20 mmol) was dissolved in tetrahydrofuran (3 mL) and 10% palladium on charcoal (65 mg) was added. The mixture was flushed thrice with nitrogen, thrice with hydrogen, and then stirred under hydrogen for 45 min. The mixture was filtered through Celite, the Celite was rinsed with ethyl acetate (10 mL), and the combined filtrates were evaporated to give 3-[2-tetrahydropyranyloxy]4-bromobutanoic acid as a colourless oil, 54 mg (98%). IR (neat): 1715 cm$^{-1}$. Mass spectrum (CI, m/z): 267, 269 (M+1, M+3).

Step 5. t-Butyl N-Hydroxyglycine. Z-Benzaldoxime (5.64 g, 46.61 mmol) and t-butyl bromoacetate (7.58 mL, 10 g, 51.27 mmol) were added successively to a solution of sodium (1.07 g, 0.047 g-atom) in 2-propanol (120 mL). The suspension was stirred for 2 h and then poured into water (100 mL). Extraction with dichloromethane, followed by drying over anhydrous magnesium sulfate and concentration gave a residue which was chromatographed on silica gel. Elution with 60% ethyl acetate-hexanes gave t-butyl N-benzylideneglycine N-oxide.

The t-butyl N-benzylideneglycine N-oxide (1.3 g, 5.53 mmol) was added to a stirred suspension of sodium methoxide (0.418 g, 7.74 mmol) and hydroxylamine hydrochloride (0.538 g, 7.74 mmol) in methanol (6 mL). The mixture was stirred at 50° C. until the solid dissolved, and the solvent was then removed. The residue was treated with dichloromethane, filtered and concentrated. The residue was chromatographed on silica gel. Elution with 60% ethyl acetate-hexanes gave t-butyl N-hydroxyglycine. Calculated for $C_6H_{13}NO_2$: C, 48.98; H, 8.84; N, 9.52. Found: C, 48.13; H, 8.65: N, 9.44.

Step 6. The product of Step 5 (85 mg, 0.32 mmol) was dissolved, under nitrogen, in methylene chloride (3 mL), the solution was cooled in an ice-bath, stirred, and dicyclohexylcarbodiimide (70 mg, 0.34 mmol) was added, followed by a solution of the product of Step 4 (46.8 mg, 0.32 mRNA) in methylene chloride (3 mL). The cloudy mixture was stirred for 5 min in the ice-bath and was then allowed to warm to room temperature. After 12 h, ether (20 mL) was added, the mixture was filtered, and the filtrate was evaporated. The residue was chromatographed on silica gel. Elution with 30:70 ethyl acetate:hexane gave the compound shown in Scheme 3 at page 9, lines 27–30, R═H.

Step 7. Protected 2-Carboxymethyl-5-Hydroxy-1,2-Oxazin-3-One. The product of Step 6 (37 mg, 0.093 mmol) was dissolved in methylene chloride (2 mL), and triethylamine (14 μL, 10.2 mg, 0.10 mmol) was added. The solution was left, under nitrogen, for 1 h, and diazabicycloundecene (DBU) (7 μL, 0.047 mmol) was added followed, after 2 h, by an additional 5.0 μL (0.33 mmol) of DBU. Stirring was continued under nitrogen for 3.2 h, and the reaction mixture was then diluted with methylene chloride (10 mL), washed with water (10 mL), dried over anhydrous sodium sulfate and evaporated. Chromatography on silica gel and elution with 45:55 ethyl acetate:hexanes gave the product as a mixture of two diastereomers. $^1$Hmr (CDCl$_3$, δ): 4.66 (1H, m, one isomer), 4.41 (1H, m, second isomer), 4.32–4.45 (2H, m, both isomers), 3.83 (1H, m, one isomer), 2.94–2.62 (2H, both isomers), 1.8 (2H, m), 1.7 (2H, m), 1.55 (2H, m), 1.47 (9H, s).

Figure 3:
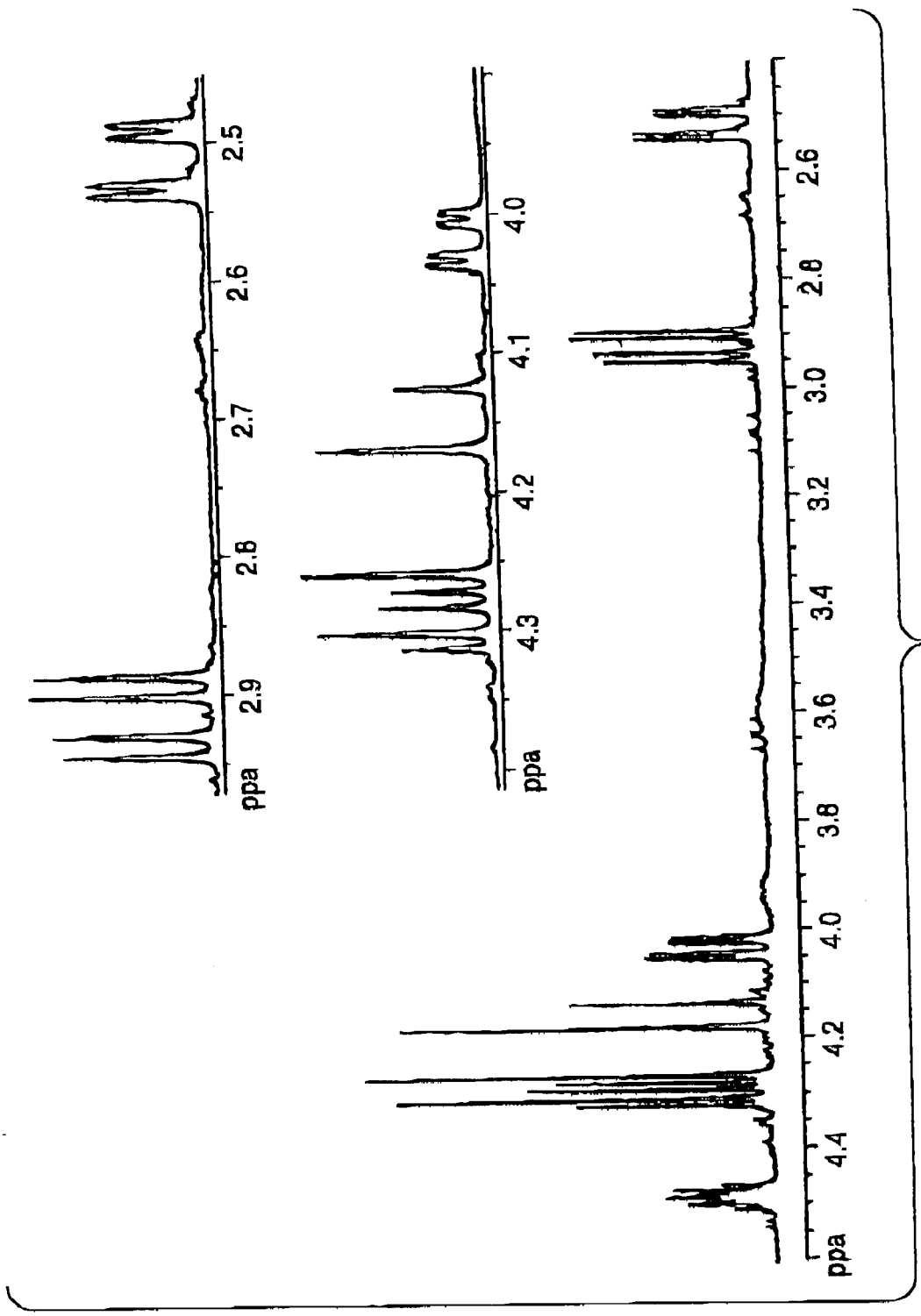
FIG. 3 is a graph of the proton nmr spectrum for 2-carboxymethyl-5-hydroxy-1,2-oxazin-3-one.
Figure 4:
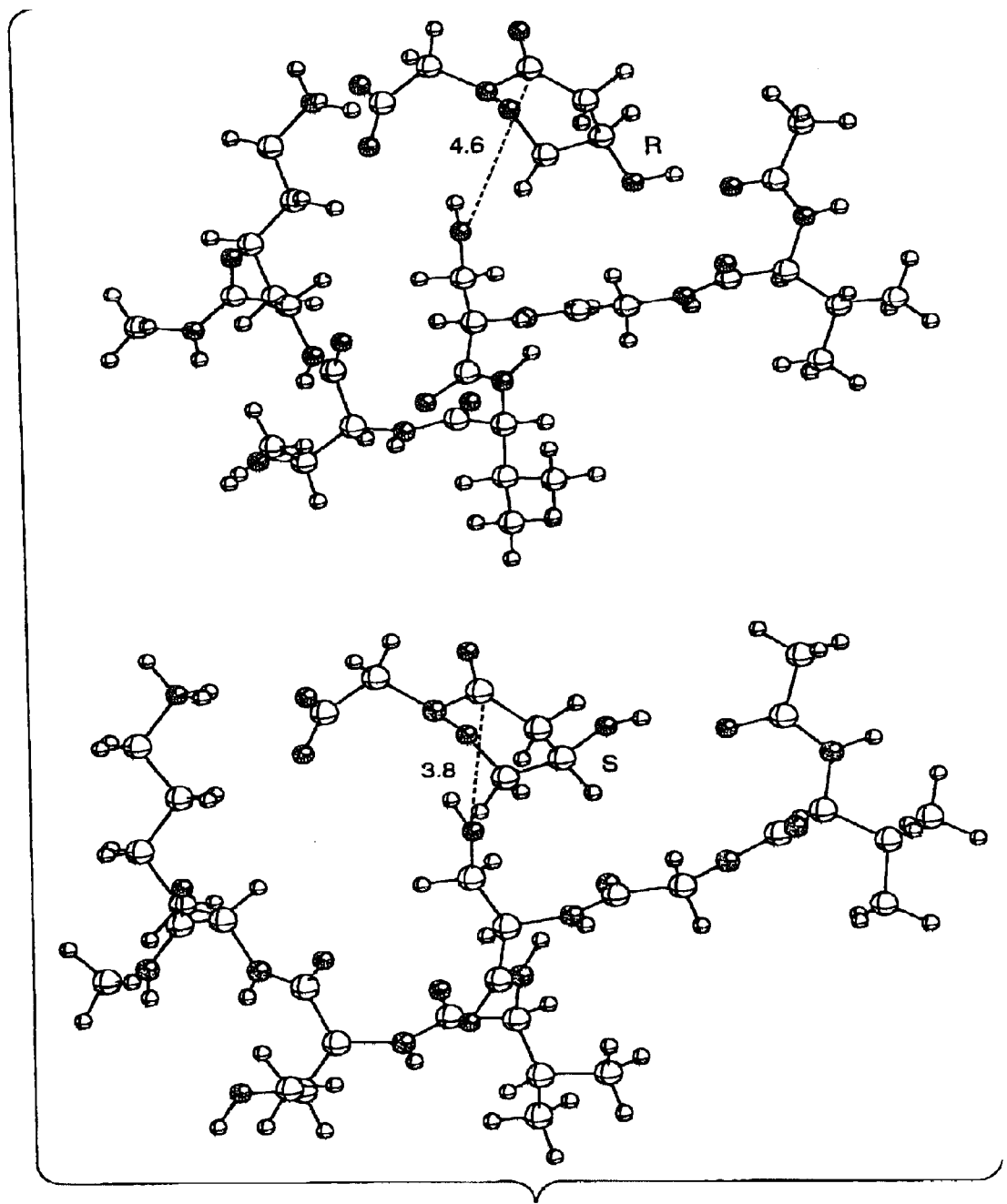
FIG. 4 is a computer drawing of the 5R and 5S enantiomers of 2-carboxymethyl-5-hydroxy-1,2-oxazin-3-one complexed to a model of the penicillin receptor.

Step 8. 2-Carboxymethyl-5-Hydroxy-1,2-Oxazin-3-one. The product of Step 7 (11 mg, 0.35 mmol was dissolved, under nitrogen, in, methylene chloride (1 mL), the solution was cooled in an ice-bath, and trifluoroacetic acid (3 mL) was added. Additional trifluoroacetic acid was added after 15 min (3 μL), after an additional 20 min (500 μL), and after an additional 30 min (300 μL). After an additional 55 min, the solvent was removed. The product was redissolved in trifluoroacetic acid (500 μL), evaporated after 30 min, and the residue was shaken with ethyl acetate (2 mL), water (1 mL) and sodium bicarbonate (3 mg). The aqueous phase was separated, washed with ethyl acetate, and lyophilized to give RS-2-carboxymethyl-5-hydroxy-1,2-oxazin-3-one as the sodium salt. $^1$Hmr (D$_2$O$_1$ δ): 4.49 (1H, m), 4.29 (1H, dd, 12.1, 4.6 Hz), 4.28 (1H, d, 18.2 Hz), 4.15 (1H, d, 18.2 Hz), 4.02 (1H, ddd, 12.1, 3.2, 0.8 Hz), 2.92 (1H, dd, 16.8, 5.9 Hz), 2.52 (1H, ddd, 16.8, 3.2 Hz). The proton nmr spectrum of this compound is shown in FIG. 3. FIG. 4 suggests that the 5S enantiomer exhibits a slightly better fit to a model of the penicillin receptor than the 5R enantiomer.

EXAMPLE 2

2-[2-Carboxypropyl]-5-hydroxy-1,2-oxazin-3-one

Step 1. t-Butyl 2-Bromopropionate. Isobutylene (2.4 g, 42.8 mmoles) was condensed into a pressure bottle at −15° C. Dioxane (6 mL) and 2-bromopropionic acid (3.5 mL, 38.9 mmoles) were added and the mixture was stirred for 5 min, warmed to −10° C., and concentrated sulfuric acid (250 μL) was added. The bottle was scaled, the reaction mixture was stirred overnight at room temperature, and the bottle was then opened and the contents poured into dichloromethane (50 mL). The solution was washed with 20% potassium carbonate (50 mL), water (50 mL), dried over anhydrous magnesium sulfate and evaporated to give t-butyl bromopropionate (2.17 g, 27%). $^1$HMR (CDCl$_3$, δ): 4.31 (1H, q, 7.1 Hz), 1.81 (3H, d, 7.1 Hz), 1.52 (9H, s).

Step 2. t-Butyl N-Benzylidenealanine N-Oxide. Z-Benzaldoxime (580 mg, 4.79 mmoles) and t-butyl 2-bromopropionate (VI–18) (980 mg), 4.69 mmoles) were added successively to a solution of sodium hydride (200 mg, of a 60% dispersion in mineral oil, 5.00 mmoles) in 2-propanol (20 mL). The suspension was stirred at room temperature for 3 h, and then poured into water and extracted with ethyl acetate (2×20 mL). The organic extract was dried over anhydrous magnesium sulfate and evaporated to give a white coloured solid. Trituration with anhydrous diethyl ether (8 mL) afforded the product (464 mg, 40%), m.p. 115–117° C. $^1$HMR (CDCl$_3$, δ): 8.26–8.23 (2H, m, Ar+HC═N$^+$), 7.43–7.41 (4H, m, Ar), 4.65 (1H, q, 7.0 Hz, α-CH), 1.73 (3H, d, 7.0 Hz, CH$_3$), 1.47 (9H, s, CO$_2$C (CH$_3$)$_3$). IR (KBr): 1736, 1582 cm$^{-1}$. Mass spectrum (CI, m/z): 250 (M+1). Calcd. for $C_{14}H_{19}N_1O_3$: C 67.45; H 7.68; N 5.62. Found: C 67.10; H 7.59; N 5.90.

Step 3. t-Butyl N-hydroxyalanine. The product of step 2 (460 mg, 185 mmoles) was added to a stirred suspension of sodium methoxide (141 mg, 2.61 mmoles) and hydroxylamine hydrochloride (182 mg, 2.62 mmoles) in dry methanol (5.5 8.69. Found: C 51.02; H 9.30; N 8.55.

Step 4. Coupling of 3-[2-Tetrahydropyranyloxy]-4-Bromobutanoic Acid with t-Butyl N-hydroxyalanine. The 3-12-tetrahydropyranyloxyl-4-bromobutanoic acid (54 mg, 0.20 mmole (as prepared in Example 1 above, step 4)) was dissolved in dichloromethane (3 mL), the solution was cooled in an ice-bath, stirred, and dicyclohexylcarbodiimide (41 mg, 0.20 mmole) was added, followed by a solution of the ester t-Butyl N-hydroxyalanine in dichloromethane (2 mL). The mixture was stirred in the ice-bath for 5 min, the ice-bath was then removed, and stirring was continued for 3 h. The mixture was filtered, and the filtrate was evaporated. The mixture was filtered, and the filtrate was evaporated. The residue was chromatographed on silica gel. Elution with ethyl acetate-hexanes (2:3) gave the compound shown in Scheme 3 at page 9, lines 27–30, R=$CH_3$ (74 mg, 54%). IR ($CH_2Cl_2$): 3432, 1736, 1657 $cm^{-1}$. Mass spectrum (CI, m/z): 410, 412 (M+1, M+3).

Step 5. t-Butyl 2-[2-Carboxypropyl]-5-[2-Tetrahydropyranyloxy]-1,2-Oxazin-3-one. The product of Step 4 (36 mg, 0.088 mmole) was dissolved in dichloromethane (10 mL), cooled in an ice-bath, and 1,8-diazobicyclo[5.4.0]undec-7-one (15 µL, 0.1 mmole) was added. The solvent was removed after 1 h. The residue was dissolved in ethyl acetate (25 mL) and the solution was washed with water (2×25 mL), dried over anhydrous magnesium sulfate and evaporated to the protected oxazinone t-butyl 2-[2-carboxypropyl]-5-[2-tetrahydropyranyloxy]-1,2-oxazin-3-one (25 mg, 85%). IR ($CH_2Cl_2$): 1736, 1678 $cm^{-1}$. Mass spectrum (CI, m/z): 330 (M+1). HRMS-CI calcd. for $C_{16}H_{27}NO_6$: 330.1917 (M+1). Found: 330.1916.

Step 6. The product of Step 5 (10.1 mg, 0.031 mmol) was dissolved in dichloromethane, the solution was cooled in an ice-bath, and trifluoroacetic acid (1 mL, 13.0 mmoles) was added. The solution was stirred for 30 min, and the solvent was then removed The residue was dissolved in trifluoroacetic acid (500 µL), and the solution was stirred at room temperature for 15 min and evaporated. The residue was shaken with ethyl acetate (3 mL) and a solution of sodium bicarbonate (2.8 mg) in water (2 mL). The aqueous phase was lyophilized to give the sodium salt of 2-[2-carboxypropyl]-5-hydroxy-1,2-oxazin-3-one as an approximately 1:1 mixture of RR/SS and RS/SR diastereomers. $^1$HMR ($D_2O$, δ): 4.89 (1H, q, 7.3 Hz, α-CH, one isomer), 4.88 (1H, q, 7.3 Hz, α-CH, second isomer), 4.72–4.69 (2H, m, H5, both isomers), 4.54 (1H, d, 10.5 Hz, H6, one isomer), 4.53 (1H, d, 10.5 Hz, H6, second isomer), 4.35 (2H, d, 10.5 Hz, H6, both isomers), 2.97 (1H, d, 18.3 Hz, H4, one isomer), 2.95 (1H, d, 18.3 Hz, H4, second isomer), 2.51 (2H, m, 18.3 Hz, H4, both isomers), 1.45 (3H, d, 7.3 Hz, $CO_2C(CH_3)_3$, one isomer), 1.42 (3H, d, 7.3 Hz, $CO_2C(CH_3)_3$, second isomer). Mass spectrum (CI, m/z, for the acid VI-1a): 190 (M+1), 172 (M+1-$H_2O$) HRMS-CI calcd. for $C_7H_{12}NO_5$: 190.0716 (M+1). Found: 190.0712.

EXAMPLE 3

Bioassay of the Product of Example 1

Figure 5:
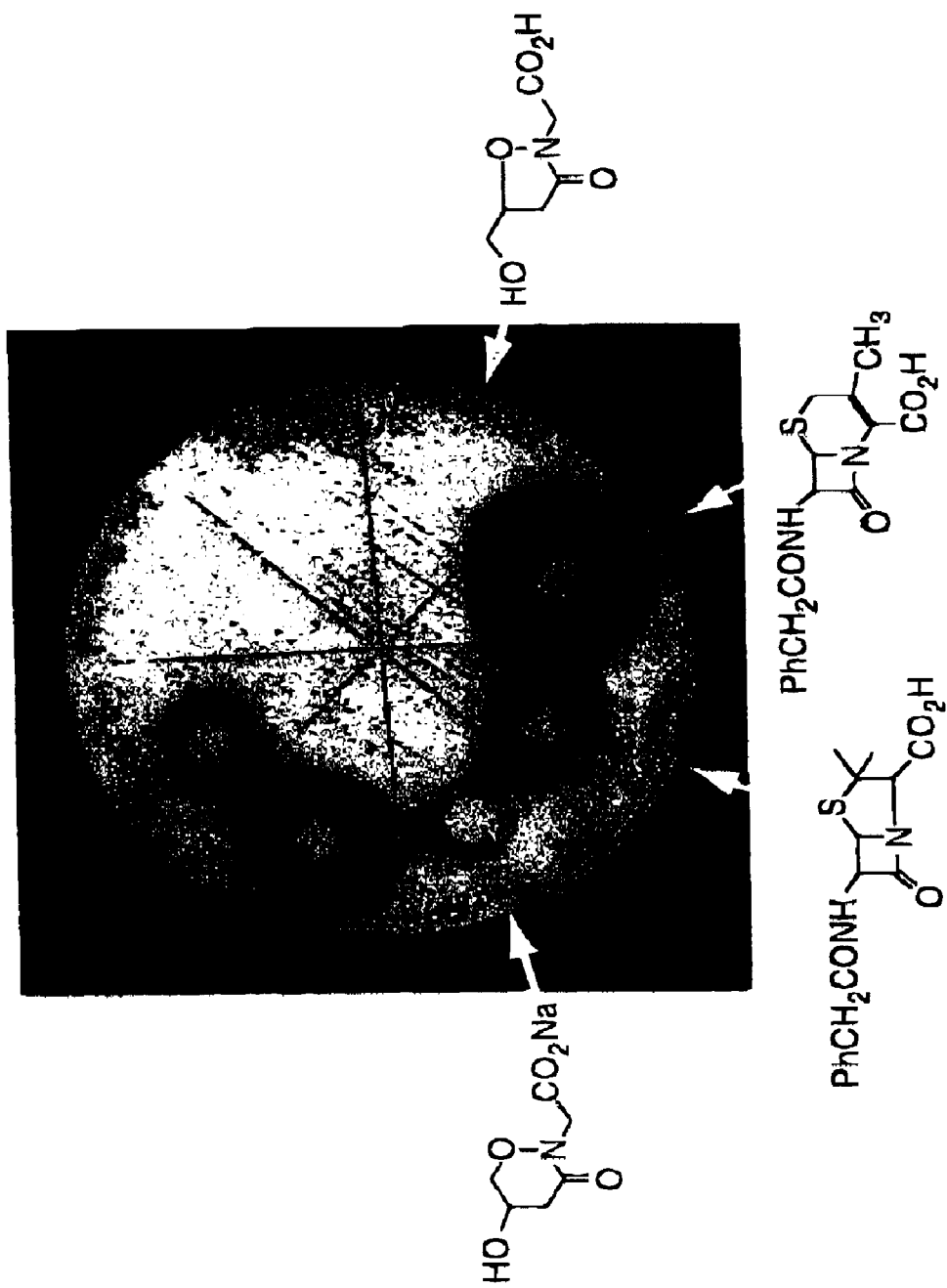
FIG. 5 is a photograph showing the results of antibacterial assays of 2-carboxymethyl-5-hydroxy-1,2-oxazin-3-one, Penicillin G and desacetoxy-cephalosporin G versus *M. luteus*.

Samples were applied to filter discs in the amounts indicated. The discs were applied to agar plates seeded with *Micrococcus luteus*, and the plates were incubated overnight at 37° C. The results are illustrated in FIG. 5 and summarized in the following Table 1:

TABLE 1

| COMPOUND | WEIGHT (micrograms) | ZONE SIZE (cm) |
|---|---|---|
| water blank |  | 0 |
| penicillin G | 0.1 | 1.6 |
| oxazinone | 100 | 1.1 |
| oxazinone | 1000 | 2.0 |

EXAMPLE 4

Bioassay of the Product of Example 2

Samples were assayed as in Example 3, with the results summarized in the following Table 2:

TABLE 2

| COMPOUND | WEIGHT (micrograms) | ZONE SIZE (cm) |
|---|---|---|
| water blank |  | 0 |
| desacetoxycephalosporin G | 2.5 | 2.5 |
| oxazinone | 12.0 | 2.0 |

Figure 2:
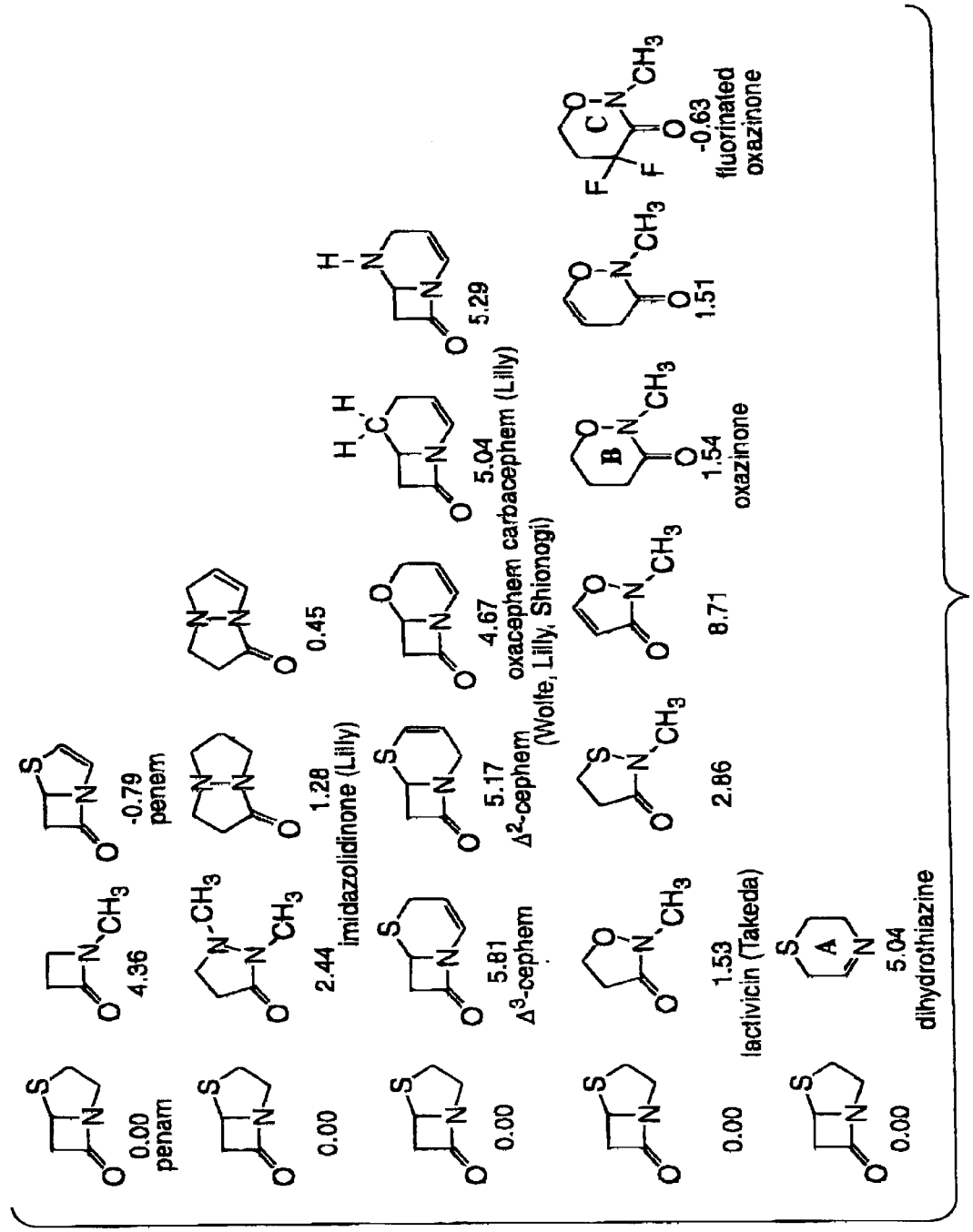
FIG. 2 is a summary of the calculated activation energies for the reactions of various ring systems with methanol, catalyzed by one water molecule, relative to the activation energy for the ring system of penicillin.

With reference to Tables 1 and 2, the bioassays suggest that the 2-carboxymethyl product of Example 1 (where R=H) exhibits weak antibacterial activity at least 1000 times less than that of penicillin. The 2-carboxyethyl analogue more closely resembles and is approximating the three-dimensional molecular structure of the D-Ala-D-Ala peptidoglycan skeleton and has approximately 50 times the activity of the carboxymethyl product. As will be apparent to one skilled in the art, the introduction and proper positioning of other substituents on the 1,2-oxazin-one ring will likely result in greater antibacterial activity. For example, the fluorinated oxazinone ring system identified in FIG. 2 by the letter C should be significantly more active than penicillin based on its low calculated activation energy. Further, some oxazinone stereoisomers may exhibit greater activity than others based on the precise nature of their fit with penicillin active site receptors.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

REFERENCES

1. Strominger, J. L.; Park, J. T.; Thompson, R. E. Composition of the cell wall of *Staphylococcus aureus*: its relation to the mechanism of action of penicillin. J. Biol. Chem. 234, 3263–3268, 1959.
2. Waxman, D. J.; Strominger, J. L. Penicillin-binding proteins and the mechanism of action of β-lactam antibiotics. Annu. Rev. Biochem. 52, 825–869, 1983.
3. Ghuysen, J.-M. Serine β-lactamases and penicillin-binding proteins. Annu. Rev. Microbiol. 45, 37–67, 1991.

4. Christensen, H.; Martin, M. T.; Waley, S. G. β-Lactamases as fully efficient enzymes. Determination of all the rate constants in the acyl-enzyme mechanism. Biochem. J. 266, 853–861, 1990.
5. Tomasz, A Multiple-antibiotic-resistant pathogenic bacteria A report on the Rockefeller University workshop. N. Engl. J. Med. 330, 1247–1251, 1994; Begley, S. The end of antibiotics. Newsweek. 46–51, Mar. 28, 1994; Chin, G. J.; Marx. J. Resistance to antibiotics. (Introduction to a series of articles in the Frontiers in Biotechnology Series). Science. 264, 359–392, 1994.
6. S. Wolfe, C. K. Kim, K. Yang, N. Weinberg, and Z. Shi. Hydration of the Carbonyl Group. A Theoretical Study of the Cooperative Mechanism. J. Am. Chem. Soc. 117, 4240–4260, 1995.
7. S. Wolfe, Z. Shi, K Yang, S. Ro, N. Weinberg and C. K. Kim Hydration of the Carbonyl Group. Further Evidence for a Cooperative Mechanism from Experimental and Theoretical Studies of the Hydrations of Formaldehyde, Acetaldehyde, Acetone and Cyclohexanone. Can. J. Chem. 76, 114–124, 1998.
8. S. Wolfe, K. Yang and M. Khalil. Conformation-activity relationships and the mechanism of action of penicillin Can. J. Chem. 66, 2733–2750, 1988.
9. Nakao, Y. Lactivicin, a new type of β-lactam-like antibiotic from bacteria: chemistry and biological activity. Recent Advances in the Chemistry of β-Lactam Antibiotics. Bentley, P. H; Southgate, R, Eds. Spec. Publ No. 70, Royal Society of Chemistry: Cambridge, pp 119–138, 1988.
10. Ternansky, R. J.; Draheim, S. E. The synthesis and biological evaluation of pyrazolidinone antibacterial agents. Recent Advances in the Chemistry of β-Lactam Antibiotics. Bentley, P. H.; Southgate, R, Eds. Spec. Publ No. 70, Royal Society of Chemistry: Cambridge, pp 139–156, 1988.
11. J. Mol. Biol. 220, 435–455 (1991).
12. J. Mol. Biol. 217, 701–719 (1991).
13. Nature, 359,700–705(1992).

What is claimed is:

1. A process for the production of a compound of the formula (I) or a pharmaceutically acceptable salt thereof, comprising condensation of a carboxyl-protected N-hydroxy alpha-amino acid with 3-hydroxy-protected-4-bromobutanoic acid, and removal of the protecting groups, wherein said compound of formula (I) is:

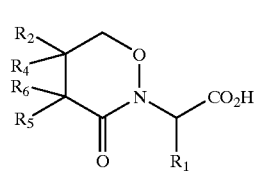

wherein R is the side chain of a D- or L-alpha amino acid, $R_2$ is OH, $NH_2$ or $NHCOR_3$; $R_3$ is a substituent known to confer antibacterial activity when present in the side chain of penicillin or cephalosporin; $R_4$ is H or lower alkyl; $R_5$ is H, OH, $NH_2$ or $NHCOR_3$; $R_6$ is H, OH, $NH_2$ or $NHCOR_3$ or $R_5$ and $R_6$ taken together comprise the oxygen of a carbonyl group.

2. The process of claim 1, wherein the carboxyl-protecting group is t-butyl.

3. The process of claim 1, wherein the amino acid has the S-configuration and the butanoic acid has the 3S-configuration.

4. The process of claim 1, wherein the amino acid has the S-configuration and the butanoic acid has the 3R-configuration.

5. The process of claim 1, wherein the amino acid has the R-configuration and the butanoic acid has the 3R-configuration.

6. The process of claim 1, wherein the amino acid has did R-configuration and the butanoic acid has the 3S-configuration.

7. A method of synthesis of a compound of formula (I) or a pharmaceutically acceptable salt thereof, wherein said compound of formula (I) is

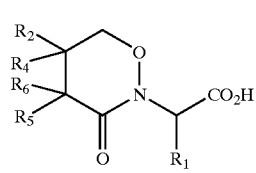

wherein $R_1$ is the side chain of a D- or L-alpha amino acid, $R_2$ is OH, $NH_2$ or $NHCOR_3$; $R_3$ is a substituent known to confer antibacterial activity when present in the side chain of penicillin or cephalosporin $R_4$ is H or lower alkyl; $R_5$ is H, OH, $NH_2$ or $NHCOR_3$; $R_6$ is H, OH, $NH_2$ or $NHCOR_3$ or $R_5$ and $R_6$ taken together comprise the oxygen of a carbonyl group, wherein said method is:

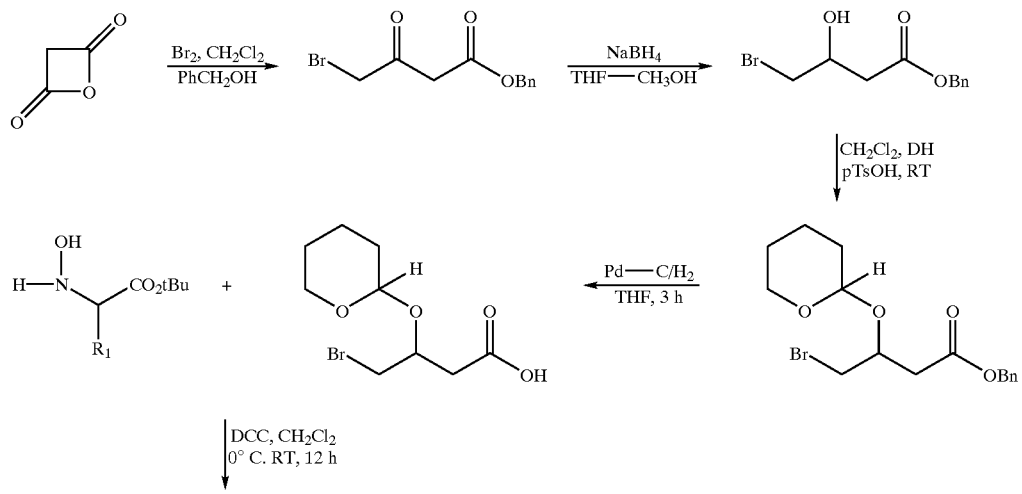

-continued

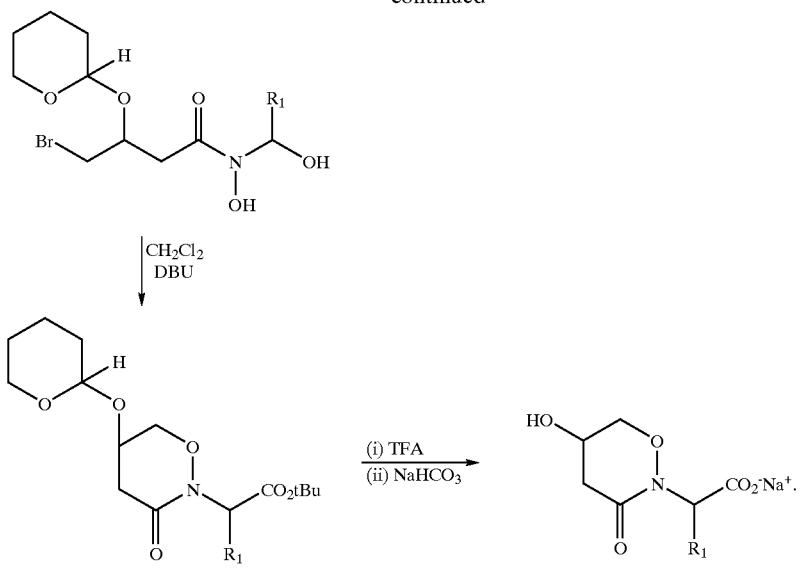

8. The process of claim 1, wherein the hydroxyl-protecting group is 2-tetrahydropyranyl.

9. The process of claim 1, wherein the condensing agent is dicyclohexylcarbodiimide.

10. The process of claim 1, wherein the cyclization is performed with an organic amine.

11. The process of claim 1, wherein the removal of the protecting groups is performed with trifluoroacetic acid.

* * * * *